United States Patent
Okada et al.

(10) Patent No.: US 6,190,700 B1
(45) Date of Patent: *Feb. 20, 2001

(54) PRODUCTION OF SUSTAINED-RELEASE PREPARATION FOR INJECTION

(75) Inventors: Hiroaki Okada; Yayoi Douken, both of Osaka; Akihiro Yamada, Kanagawa, all of (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/766,612

(22) Filed: Dec. 13, 1996

(30) Foreign Application Priority Data

Dec. 15, 1995 (JP) .................................................. 7-327689

(51) Int. Cl.⁷ .......................................................... A61K 9/52
(52) U.S. Cl. ........................... 424/499; 424/489; 424/501; 514/2; 514/964
(58) Field of Search .................................. 424/489, 499, 424/501; 514/2, 964

(56) References Cited

U.S. PATENT DOCUMENTS

| | | | |
|---|---|---|---|
| 4,722,943 | * | 2/1988 | Melber ..................................... 521/57 |
| 5,514,670 | * | 5/1996 | Friedman .................................. 514/2 |

FOREIGN PATENT DOCUMENTS

| | | |
|---|---|---|
| 0 145 240 | 6/1985 | (EP) . |
| 0 190 833 | 8/1986 | (EP) . |
| 0 442 671 A2 | 8/1991 | (EP) . |
| 0 535 937 A1 | 4/1993 | (EP) . |
| 0 582 459 A2 | 2/1994 | (EP) . |
| 0 586 238 A2 | 3/1994 | (EP) . |
| 0 761 213 A2 | 3/1997 | (EP) . |
| 89/04673 | 6/1989 | (WO) . |

* cited by examiner

Primary Examiner—Gollamudi S. Kishore
(74) Attorney, Agent, or Firm—Wenderoth, Lind & Ponack, L.L.P.

(57) ABSTRACT

Disclosed is a method of producing a sustained-release preparation for injection, which comprises adding to microspheres which are obtained from w/o emulsion with a solution containing a physiologically active peptide as an internal aqueous phase and a solution containing a polylactic acid having a weight-average molecular weight of about 5,000 to about 25,000 as an oil phase, a sugar in an amount of about 2 to about 60% (w/w) relative to the microspheres; freeze drying and subsequent heating at the temperature ranging from the glass transition temperature of the microspheres to the temperature which is higher by about 20° C. than the glass transition temperature for about 24 to about 120 hours; and the method of the present invention suppresses microsphere particle aggregation during production process, makes it possible to almost perfectly remove the water and organic solvent in microspheres, and yields microspheres having good dispersibility and storage-stability.

3 Claims, No Drawings

PRODUCTION OF SUSTAINED-RELEASE PREPARATION FOR INJECTION

The present invention relates to production of a sustained-release preparation for injection.

BACKGROUND OF THE INVENTION

Microsphere type sustained-release drug preparations incorporating a biodegradable polymer are disclosed in, for example, Japanese Patent Unexamined Publication Nos. 118512/1982, 150609/1982, 100516/1985 (EP-A145240), 201816/1987 (EP-A190833), 233926/1988, 42420/1989, 032302/1991, 321622/1922 (EP-A442671), 70363/1993, 112468/1993, 194200/1993 (EP-A535937), 145046/1994 (EP-A582459) and 192068/1994 (EP-A586238). Japanese Patent Unexamined Publication Nos. 100516/1985 and 201816/1987, in particular, disclose a method of preparing sustained-release microspheres of a water-soluble physiologically active substance with high entrapment ratio and high dispersibility by the in-water drying method.

With regard to microsphere type sustained-release drug preparations incorporating a biodegradable polymer, it is necessary to prepare fine particles of uniform microsphere particle form, to ensure satisfactory dispersibility and needle passability during administration, and to prevent aggregation and particle binding from market delivery to use. Also, in the preparation method involving the use of an organic solvent, the residual solvent in the finished preparation is problematic from the viewpoint of preparation stability and safety to the human body, necessitating perfect solvent removal during the production process.

SUMMARY OF THE INVENTION

Through intensive investigation to resolve the above problems, the present inventors found it possible to almost perfectly remove the residual organic solvent and prevent particle binding to produce sustained-release microspheres of good dispersibility, needle passability and storage stability, by heating the sustained-release microspheres in the presence of sugars during freeze drying, and to suppress particle binding during drying, and enable drying at high temperatures exceeding the glass transition temperature of microsphere, to almost perfectly remove the water and solvent during freeze drying by adding sugars.

Accordingly, the present invention relates to a method of producing a sustained-release preparation for injection, which comprises adding to microspheres which are obtained from w/o emulsion with a solution containing a physiologically active peptide as an internal aqueous phase and a solution containing a polylactic acid having a weight-average molecular weight of about 5,000 to about 25,000 as an oil phase, a sugar in an amount of about 2 to about 60% (w/w) relative to the microspheres; freeze drying and subsequent heating at the temperature ranging from the glass transition temperature of the microspheres to the temperature which is higher by about 20° C. than the glass transition temperature for about 24 to about 120 hours.

DETAILED DESCRIPTION OF THE INVENTION

In the present specification, abbreviations for amino acids, protecting groups and others are based on abbreviations specified by the IUPAC-IUB Commission on Biochemical Nomenclature or abbreviations in common use in relevant fields. When an optical isomer may be present in amino acid, it is of the L-configuration, unless otherwise stated.

Abbreviations used in the present specification are defined as follows:

NAcD2Nal: N-acetyl-D-3-(2-naphthyl)alanyl
D4ClPhe: D-3-(4-chlorophenyl)alanyl
D3Pal: D-3-(3-pyridyl)alanyl
NMeTyr: N-methyltyrosyl
DLys(Nic): D-(epsilon-N-nicotinoyl)lysyl
Lys(Nisp): (Epsilon-N-isopropyl)lysyl
DhArg(Et$_2$): D-(N,N'-diethyl)homoarginyl The physiologically active peptide is preferably one consisting of 2 or more amino acids and having a molecular weight of about 200 to about 80,000. The physiologically active peptide is preferably LH-RH (luteinizing hormone-releasing hormone) agonist or LH-RH antagonist. Examples of the LH-RH agonist include a peptide represented by the formula:

$$\text{(Pyr)Glu-R}_1\text{-Trp-Ser-R}_2\text{-R}_3\text{-R}_4\text{-Arg-Pro-R}_5 \quad \text{(I)}$$

wherein $R_1$ represents His, Tyr, Trp or p-NH$_2$-Phe; $R_2$ represents Tyr or Phe; $R_3$ represents Gly or a D-type amino acid residue; $R_4$ represents Leu, Ile or Nle; $R_5$ represents Gly-NH-$R_6$ ($R_6$ is H or an alkyl group with or without a hydroxyl group) or NH-$R_7$ ($R_7$ is H, an alkyl group with or without an amino or a hydroxyl group, or ureido (—NH—CO—NH$_2$)); [hereafter also referred to as peptide (I)] or a salt thereof.

With respect to the formula (I) above, the D-type amino acid residue in $R_3$ is exemplified by α-D-amino acids having up to 9 carbon atoms (e.g., D-Leu, Ile, Nle, Val, Nval, Abu, Phe, Phg, Ser, Thr, Met, Ala, Trp, α-Aibu). These amino acid residues may optionally have a substituent (e.g., tert-butyl, tert-butoxy, tert-butoxycarbonyl, methyl, dimethyl, trimethyl, 2-naphthyl, indoly-3-yl, 2-methyl-indolyl, benzyl-imidazo-2-yl) as appropriate.

In the formula (I), the alkyl group in $R_6$ or $R_7$ is preferably a $C_{1-4}$ alkyl group. Examples of the alkyl group include methyl, ethyl, propyl, isopropyl, butyl, isobutyl, sec-butyl and tert-butyl.

Examples of the salt of the peptide represented by the formula (I) include acid salts (e.g., carbonate, bicarbonate, acetate, trifluoroacetate, propionate, succinate) and metal complex compounds (e.g., copper complex, zinc complex).

Peptide (I) or a salt thereof can be produced, for example, by a method which is described in U.S. Pat. Nos. 3,853,837, 4,008,209 and 3,972,859, British Patent No. 1,423,083, Proceedings of the National Academy of Science of the United States of America, Vol. 78, pp. 6509–6512 (1981), or an analogous method thereto.

Peptide (I) is preferably the following (a) to (j). (a) leuprorelin [a peptide represented by the formula (I) wherein $R_1$ is His, $R_2$ is Tyr, $R_3$ is D-Leu, $R_4$ is Leu, and $R_5$ is NHCH$_2$—CH$_3$];
(b) Gonadrelin

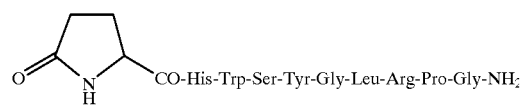

(German Patent No. 2213737); (c) Buserelin

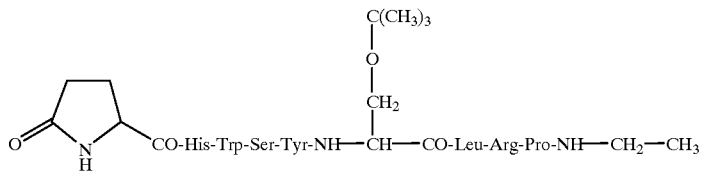
(U.S. Pat. No. 4,024,248, German Patent No. 2438352, Japanese Patent Unexamined Publication No 41359/1976); (d) Triptorelin
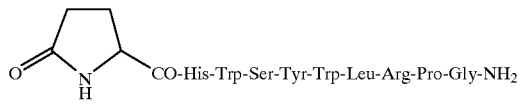
(U.S. Pat. No. 4,010,125, Japanese Patent Unexamined Publication No. 31073/1977); (e) Goserelin
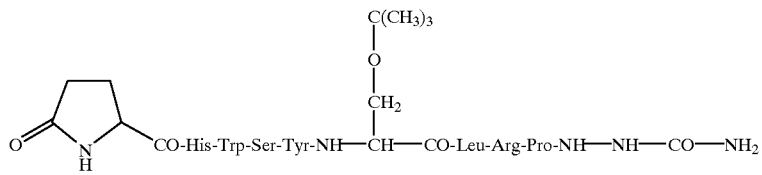
(U.S. Pat. No. 4,100,274, Japanese Patent Unexamined Publication No. 136172/1977); (f) Nafarelin
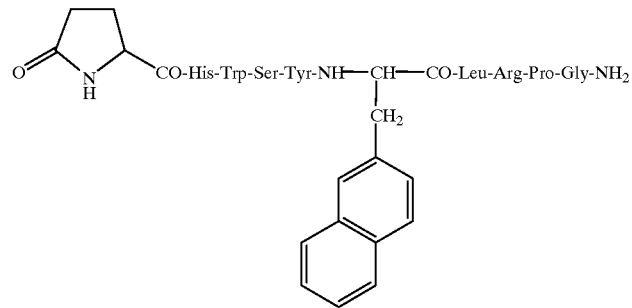
(U.S. Pat. No. 4,234,571, Japanese Patent Unexamined Publication Nos. 164663/1980, 264498/1988 and 25794/1989; (g) Histrelin
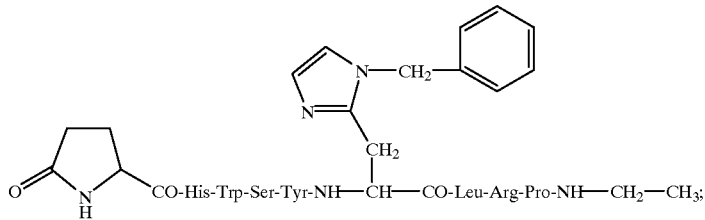

(h) Deslorelin

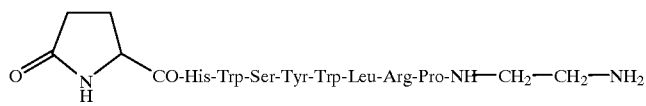

(U.S. Pat. Nos. 4,569,967 and 4,218,439); (i) Meterelin

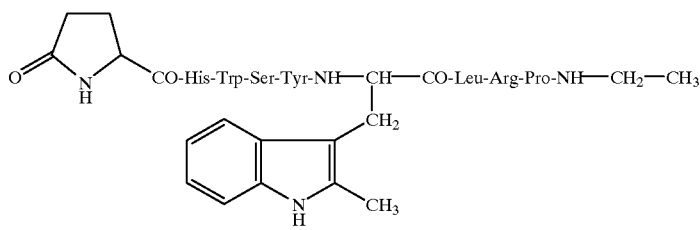

(WO9118016); (j) Lecirelin

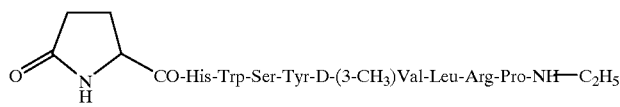

(Belgium Patent No. 897455, Japanese Patent Unexamined Publication No. 59654/1984).

In the above-described formulae (c) to (j), an amino acid which corresponds to $R_3$ in the formula (I) is of D-configuraiton.

Peptide (I) or a salt thereof is especially preferably leuprorelin or leuprorelin acetate.

Examples of the LH-RH antagonist include those disclosed in U.S. Pat. Nos. 4,086,219, 4,124,577, 4,253,997 and 4,317,815, or a peptide represented by the formula:

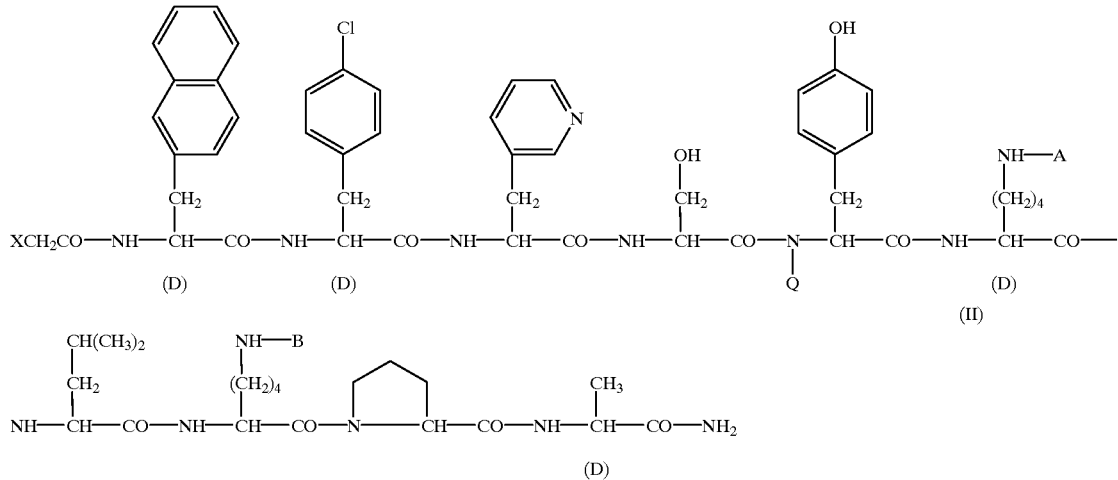

wherein X represents hydrogen atom or tetrahydrofurylcarboxamide; Q represents hydrogen atom or methyl; A represents nicotinoyl or N,N'-diethylamidino; B represents isopropyl or N,N'-diethylamidino; (hereafter also referred to as peptide (II)) or a salt thereof.

With respect to the formula (II), X is preferably tetrahydrofurylcarboxamide, more preferably (2S)-tetrahydrofurylcarboxamide. Also, A is preferably nicotinoyl; B is preferably isopropyl.

When peptide (II) has one or more kinds of asymmetric carbon atoms, two or more optical isomers are present. Such optical isomers and mixtures thereof are also included in the scope of the present invention.

Peptide (II) or a salt thereof can be produced by per se known methods. Such methods include the methods described in Japanese Patent Unexamined Publication No.

101695/1991 and the Journal of Medicinal Chemistry, Vol. 35, p. 3942 (1992) and other publications, and similar methods.

The salt of peptide (II) is preferably a pharmacologically acceptable salt. Such salts include salts formed with inorganic acids (e.g., hydrochloric acid, sulfuric acid, nitric acid), organic acids (e.g., carbonic acid, bicarbonic acid, succinic acid, acetic acid, propionic acid, trifluoroacetic acid) etc. More preferably, the salt of peptide (II) is a salt formed with an organic acid (e.g., carbonic acid, bicarbonic acid, succinic acid, acetic acid, propionic acid, trifluoroacetic acid), with greater preference given to a salt formed with acetic acid. These salts may be mono- through tri-salts.

Preferable examples of peptide (II) or a salt thereof are given below.

(1) 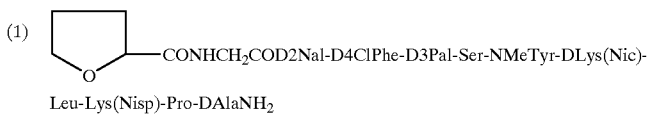
Leu-Lys(Nisp)-Pro-DAlaNH$_2$ (the S-isomer of this peptide is referred to as compound A)

(2) 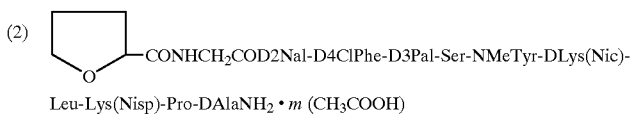
Leu-Lys(Nisp)-Pro-DAlaNH$_2$ • $m$ (CH$_3$COOH)

wherein m represents a real number of 1 to 3.
(3) NAcD2Nal-D4ClPhe-D3Pal-Ser-Tyr-DhArg(Et$_2$)-Leu-hArg(Et$_2$)-Pro-DAlaNH$_2$
(4) NAcD2Nal-D4ClPhe-D3Pal-Ser-Tyr-DhArg(Et$_2$)-Leu-hArg(Et$_2$)-Pro-DAlaNH$_2$·n(CH$_3$COOH) wherein n represents a real number of 1 to 3.

Peptide (II) or a salt thereof is especially preferably (1) or (2) above.

Examples of physiologically active peptides include insulin, somatostatin, somatostatin derivative (Sandostatin; see U.S. Pat. Nos. 4,087,390, 4,093,574, 4,100,117 and 4,253,998), growth hormones, prolactin, adrenocorticotropic hormone (ACTH), ACTH derivatives (e.g., ebiratide), melanocyte-stimulating hormone (MSH), thyrotropin-releasing hormone [represented by the structural formula (Pyr)Glu-His-ProNH$_2$, hereinafter also referred to as TRH] and salts and derivatives thereof (see Japanese Patent Unexamined Publication Nos. 121273/1975 and 116465/1977), thyroid-stimulating hormone (TSH), luteinizing hormone (LH), follicle-stimulating hormone (FSH), vasopressin, vasopressin derivative [desmopressin, see Folia Endocrinologica Japonica, Vol. 54, No. 5, pp. 676–691 (1978)], oxytocin, calcitonin, parathyroid hormone (PTH), glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, interferons (e.g., α-, β- and γ-interferons), interleukins (e.g., 1, 2, 3, 4, 5, 6, 7, 8, 9, 10, 11 and 12), tuftsin, thymopoietin, thymosin, thymostimulin, thymic humoral factor (THF), blood thymic factor (FTS) and derivative thereof (see U.S. Pat. No. 4,229,438), other thymic factors [Igaku no Ayumi, Vol. 125, No. 10, pp. 835–843 (1983)], tumor necrosis factor (TNF), colony-stimulating factors (e.g., CSF, GCSF, GMCSF, MCSF), motilin, dynorphin, bombesin, neurotensin, caerulein, bradykinin, urokinase, asparaginase, kallikrein, substance P, insulin-like growth factors (IGF-I, IGF-II), nerve growth factor (NGF), cell growth factors (e.g., EGF, TGF-α, TGF-β, PDGF, acidic FGF, basic FGF), bone morphogenic factor (BMP), nerve nutrition factors (e.g., NT-3, NT-4, CNTF, GDNF, BDNF), blood coagulation factors VIII and IX, lysozyme chloride, polymixin B, colistin, gramicidin, bacitracin, erythropoietin (EPO), thrombopoietin (TPO), and endothelin-antagonistic peptides (see European Patent Publication Nos. 436189, 457195 and 496452, and Japanese Patent Unexamined Publication Nos. 94692/1991 and 130299/1991).

The physiologically active peptide may be used as such or as a pharmacologically acceptable salt (e.g., salts formed with inorganic acids such as hydrochloric acid, sulfuric acid and nitric acid, and salts formed with organic acids such as carbonic acid and succinic acid, when the drug has a basic group such as the amino group; salts formed with inorganic bases exemplified by alkali metals such as sodium and potassium, salts formed with organic base compounds exemplified by organic amines such as triethylamine, and basic amino acids such as arginine, when the drug has an acidic group such as the carboxy group).

Although the polylactic acid may be of the D- or L-configuration or a mixture thereof, it is preferable that the ratio of the D-/L-configuration (mol%) falls within the range from about 75/25 to about 20/80. The ratio of the D-/L-configuration (mol %) is more preferably about 60/40 to about 25/75, and still more preferably about 55/45 to about 25/75.

The weight-average molecular weight of said polylactic acid is preferably about 5,000 to about 25,000, more preferably about 10,000 to about 20,000. Also, the degree of dispersion of the polylactic acid is preferably about 1.2 to about 4.0, more preferably about 1.5 to about 3.5.

The polylactic acid can be produced by ring-opening polymerization of lactide, a dimer of lactic acid; dehydration condensation polymerization of lactic acid; or an analogous method thereto. For obtaining a polylactic acid of relatively low molecular weight for the present invention, direct dehydration condensation polymerization of lactic acid is preferred. Such a method, for example, can be carried out in accordance with the method described in Japanese Patent Unexamined Publication No. 28521/1986 or a method similar thereto.

Regarding the polylactic acid, weight-average molecular weight is in terms of polystyrene as determined by gel permeation chromatography (GPC) using 9 polystyrenes as reference substances with weight-average molecular weights of 120,000, 52,000, 22,000, 9,200, 5,050, 2,950, 1,050, 580 and 162, respectively, and degree of dispersion is one calculated therefrom. The above determination was carried out using a GPC column KF804Lx2 (produced by Showa Denko) and an RI monitor L-3300 (produced by Hitachi, Ltd.), with chloroform as a mobile phase.

Microspheres of the present invention are not limited as long as they are fine particles (microspheres) comprising a physiologically active peptide (hereafter also referred to as drug) and a polylactic acid. Examples of microspheres include microcapsules containing one drug core in each particle, multiple-core microcapsules containing a large number of drug cores in each particle, fine particles wherein the drug in a molecular form is dissolved or dispersed in the polylactic acid as a solid solution, etc.

Microspheres of the present invention can be produced by subjecting a w/o emulsion with a solution containing a physiologically active peptide as an internal aqueous phase and a solution containing a polylactic acid having a weight-average molecular weight of about 5,000 to about 25,000 as an oil phase, to a known microencapsulation method which is exemplified by a microencapsulation method by the in-water drying method, the phase separation method, and the spray drying method, or a modification thereof.

The above-described w/o emulsion is produced, for example, as given below.

First, the drug is dissolved or dispersed in water. It is recommended that the drug concentration in the aqueous solution or dispersion be set at 0.001 to 90% (w/w), preferably 0.01 to 80% (w/w). In this solution, a drug-retaining substance exemplified by gelatin, agar, sodium alginate, polyvinyl alcohol or a basic amino acid such as arginine, histidine and lysine, is added and dissolved or suspended to yield an internal aqueous phase, for the purpose of increasing the rate of drug incorporation in microspheres. The amount of drug-retaining substance added is normally 0.01 to 100 times by weight, preferably 0.05 to 50 times by weight, the amount of drug. These drug-retaining substance may be previously dissolved to optionally chosen concentrations together with the drug and filtered through a sterilizing filter, then freeze dried and stored, and dissolved freshly before use.

The internal aqueous phase may be supplemented with a pH regulator for retaining drug stability or solubility, such as carbonic acid, acetic acid, oxalic acid, citric acid, phosphoric acid, hydrochloric acid, sodium hydroxide, arginine, lysine or a salt thereof. In addition, as stabilizers for the drug, albumin, gelatin, citric acid, sodium ethylenediaminetetraacetate, dextrin, sodium hydrogen sulfite, polyol compounds (e.g., polyethylene glycol), p-oxybenzoates (e.g., methyl paraben, propyl paraben), benzyl alcohol, chlorobutanol etc., may be added.

The internal aqueous phase may be a solution, a suspension or a dispersion, which sometimes is referred to briefly as a solution throughout the present specification.

The internal aqueous phase thus obtained is added to a solution (oil phase) containing a polylactic acid followed by emulsification, to yield a w/o emulsion. This emulsification is achieved by a known dispersing method, such as the intermittent shaking method, the method using a mechanical stirrer, such as a propeller stirrer or a turbine stirrer, the colloidal mill method, the homogenizer method and the ultrasonication method.

The above-described solution (oil phase) containing a polylactic acid is prepared by dissolving said polylactic acid in an organic solvent. Any organic solvent serves this purpose, as long as it has a boiling point not higher than about 120° C., is immiscible with water and dissolves the polylactic acid. Such solvents include halogenated hydrocarbons (e.g., dichloromethane, chloroform, chloroethane, dichloroethane, trichloroethane, carbon tetrachloride), fatty acid esters (e.g., ethyl acetate, butyl acetate), ethers (e.g., ethyl ether, isopropyl ether) and aromatic hydrocarbons (e.g., benzene, toluene, xylene), with preference given to dichloromethane. These solvents may be used in combination at appropriate ratios. This polylactic acid solution in an organic solvent is normally used after sterilizing filtration with a filter preceding the following emulsification process. Although depending on stability of the polylactic acid, this polylactic acid solution in an organic solvent may be stored in a closed container at room temperature or in a cold place.

Although varying depending on kind and molecular weight of a polylactic acid and kind of an organic solvent, the polylactic acid concentration in the organic solvent solution is normally 0.01 to 90% (w/w), preferably 0.1 to 80% (w/w). It is recommended that the polylactic acid be dissolved so that no portion remains undissolved.

The mixing ratio of the aqueous drug solution or dispersion (internal aqueous phase) and the solution containing a polylactic acid (oil phase) is normally 0.1 to 1000 parts by weight, preferably 1 to 100 parts by weight of the oil phase per part by weight of the internal aqueous phase. Although varying depending on kind of drug, desired pharmacological action, duration of action and other factors, the ratio of a drug to a polylactic acid is normally about 0.01 to about 50% (w/w), preferably about 0.5 to about 40% (w/w), and more preferably about 0.1 to about 30% (w/w).

Next, the w/o emulsion thus prepared is subjected to microencapsulation process, i.e. a process wherein a solvent is removed from the emulsion to yield microspheres.

When the w/o emulsion is microencapsulated by the in-water drying method, said w/o emulsion is further added to another aqueous phase (third phase) to yield a w/o/w triple emulsion, followed by solvent evaporation from the oil phase, to yield microspheres.

An emulsifier may be added to the above-described external aqueous phase. Any emulsifier can be used, as long as it generally produces a stable o/w emulsion. Such emulsifiers include anionic surfactants (e.g., sodium oleate, sodium stearate, sodium lauryl sulfate), nonionic surfactants [e.g., polyoxyethylene sorbitan fatty acid esters (Tween 80, Tween 60; Atlas Powder), polyoxyethylene castor oil derivatives (HCO-60, HCO-70; Nikko Chemicals)], polyvinyl alcohol, polyvinylpyrrolidone and gelatin. These emulsifiers may be used in combination in an appropriate ratio. The emulsifier concentration can be chosen over the range from about 0.01 to 20% as appropriate, and is preferably used over the range from about 0.05 to 10%.

Solvent evaporation from the oil phase can be achieved by commonly used methods, including the method in which the solvent is evaporated under normal or gradually reduced pressure during stirring using a propeller stirrer, magnetic stirrer or the like, and the method in which the solvent is evaporated while the degree of vacuum and temperature are adjusted using a rotary evaporator or the like.

The thus-obtained microspheres are centrifuged or filtered to separate them, and subsequently washed with distilled water several times repeatedly to remove the free drug, drug-retaining substance, emulsifier etc. adhering to the microsphere surface.

Also, when the drug dissolves in an oil phase consisting of a water-insoluble solvent (e.g., dichloromethane, chloroform, dichloroethane, carbon tetrachloride, ethyl acetate, cyclohexane) and at least one water-miscible organic solvent (e.g., methanol, ethanol, n-propyl alcohol, isopropanol, dimethyl sulfoxide, acetonitrile), or in an oil phase consisting of a polylactic acid solution in the above-described water-insoluble solvent, or an oil phase prepared by adding at least one glycerol fatty acid ester or propylene glycol fatty acid ester to the above-described water-insoluble solvent; this oil phase may be dispersed in an aqueous phase used in the in-water drying method involving the use of the above-described w/o/w emulsion to yield an o/w emulsion, followed by the in-water drying method, to yield microspheres.

For producing microspheres by the phase separation method, a coacervating agent is gradually added to the above-described w/o emulsion while the emulsion is stirred, to precipitate and solidify the polylactic acid. Any coacervating agent can be used, as long as it is a polymeric, mineral oil or vegetable oil compound miscible with the solvent for the polylactic acid and that does not dissolve the polylactic acid. Such coacervating agents include silicon oil, sesame oil, soybean oil, corn oil, cotton seed oil, coconut oil, linseed oil, mineral oil, n-hexane and n-heptane. These may be used in combination of two or more kinds.

The thus-obtained microspheres are filtered to separate them, after which they are repeatedly washed with hexane, heptane etc. and heated to remove the coacervating agent.

If necessary, in the same manner as with the above-described in-water drying method, miocrospheres are washed with distilled water several times repeatedly to remove the free drug, drug-retaining substance etc. adhering to the microsphere surface.

For producing microcapsules by the spray drying method, the above-described w/o emulsion is sprayed via a nozzle into the drying chamber of a spray drier to volatilize the organic solvent and water in the fine droplets in a very short time, to yield fine microspheres.

If necessary, in the same manner as with the above-described in-water drying method, the thus-obtained microspheres are washed with distilled water several times repeatedly to remove the free drug, drug-retaining substance etc. adhering to the microsphere surface.

The mean particle diameter of microspheres in the present invention is chosen over the range in which the requirements concerning the degree of dispersion and needle passability are met when the microspheres are used in the form of an injectable suspension. For example, mean diameter falls within the range from about 1 to about 300 $\mu$m, preferably about 5 to about 100 $\mu$m.

The sustained-release preparation for injection of the present invention is produced by adding to the thus-obtained microspheres a sugar in an amount of about 2 to about 60% (w/w) relative to the microspheres, followed by freeze drying and subsequent heating at the temperature ranging from the glass transition temperature of the microspheres to the temperature which is higher by about 20° C. than the glass transition temperature for about 24 to about 120 hours.

Examples of the sugars used for the present invention include D-mannitol, sodium alginate, fructose, dextran, dextrin, sucrose, D-sorbitol, lactose, glucose, maltose, starches and trehalose. These sugars may be used singly or in mixture as appropriate. Of these sugars, D-mannitol, which is easy to freeze dry and low in toxicity, is most preferable.

The manner of adding a sugar is not especially limited. Examples of the manner include a method in which microspheres are thoroughly dispersed in a solution of the sugar, and a method in which the sugar is added to microspheres followed by mixing them using a mechanical mixer or the like. The amount of sugars to be added is preferably from about 5 to about 40% (w/w) relative to the microspheres. When microcapsules have already been mixed with the sugars, e.g., when the sugars have already been used and mixed during or before in-water drying or spray drying, the sugars may be additionally added so that the total amount falls within the above-mentioned range, in consideration of the previously added amount.

Freeze drying process is carried out in accordance with a known method.

The heating temperature preferably ranges from the glass transition temperature of the microspheres to the temperature which is higher by about 10° C. than the glass transition temperature. Heating is normally conducted over the product temperature range of about 30 to about 60° C.

The glass transition temperature is defined as the intermediate glass transition point obtained using a differential scanning calorimeter (DSC) when the temperature is increased at a rate of 10 or 20° C. per minute.

Heating time more preferably ranges from about 24 to about 72 hours.

Heating temperature, heating time, degree of drying and method of heating are determined according to microsphere particle diameter, stability, glass transition temperature, melting point and likelihood of melt adhesion and deformation, stability of drug contained therein, kind and amount of a sugar added thereto, and microsphere dispersibility.

Such heating effects more complete removal of water and organic solvent in microspheres.

The amount of drug in the sustained-release preparation for injection in the present invention is variable according to the kind of drug, dosage form, target disease etc., and it is normally about 0.001 mg to about 5 g, preferably about 0.01 mg to about 2 g, per unit of preparation.

As the sustained-release preparation for injection in the present invention, use is made of microspheres which are supplemented with a sugar, freeze dried and then heated (hereafter also referred to as microsphere powders) as such or as a product which is prepared by dispersing at the time of use microsphere powders in an aqueous dispersant or an oily dispersant.

Examples of the aqueous dispersant include a solution which is prepared by dissolving in distilled water an isotonizing agent (e.g., sodium chloride, glucose, D-mannitol, sorbitol, glycerol), a dispersing agent (e.g, Tween 80, HCO-50, HCO-60 (produced by Nikko Chemicals), carboxymethyl cellulose, sodium alginate), a preservative (e.g., benzyl alcohol, benzalkonium chloride, phenol), a soothing agent (e.g., glucose, calcium gluconate, procaine hydrochloride) etc. Examples of the oily dispersant include olive oil, sesame oil, peanut oil, soybean oil, corn oil, and middle-chain fatty acid glycerides.

The sustained-release preparation for injection in the present invention may be loaded into a chamber of a pre-filled syringe. Also, the above-described microsphere powders and dispersants may be loaded separately into a different chamber of Double-Chamber Pre-filled Syringe (DPS) which is a pre-filled syringe having two chambers.

The sustained-release preparation for injection in the present invention is of low toxicity and can be used safely.

Although varying depending on kind and content of drug as an active ingredient, dosage form, duration of drug release, subject animal species (e.g., warm-blooded mammals such as mice, rats, horses, bovines and humans), and purpose of administration, the dose of the sustained-release preparation for injection in the present invention may be set at any level, as long as the active ingredient is effective. The dose of the preparation per administration can be chosen as appropriate over the range from about 1 mg to about 10 g, preferably from about 10 mg to about 2 g per adult (weight 50 kg). When the above-described dispersant is used, the volume of the dispersant can be chosen as appropriate over the range from about 0.5 to about 3 ml.

The sustained-release preparation for injection in the present invention is administered to subject animal species, for example, intramuscularly or subcutaneously.

In the present invention, when a physiologically active peptide is, for example, peptide (I), (II), or a salt thereof, a sustained-release preparation for injection is useful as a preparation for treatment or prophylaxis of hormone-dependent diseases such as prostatic cancer, prostatic hypertrophy, breast cancer, endometriosis, myoma of the uterus, and neurogenic precocious puberty, or a contraceptive.

Especially, when a physiologically active peptide in the sustained-release preparation for injection of the present invention is peptide (I) or a salt thereof and the preparation is used as a preparation for treatment or prophylaxis of the above-described diseases, the dose of the preparation per administration in terms of peptide (I) or a salt thereof ranges preferably from about 1 to about 100 mg, more preferably from about 1 to about 10 mg per adult (weight 50 kg).

The present invention is hereinafter described in more detail by means of the following reference examples, examples, and experimental examples, which are not to be construed as limitative, as long as they fall within the scope of the present invention. Unless otherwise specified, % means % by weight.

REFERENCE EXAMPLE 1

200 ml of distilled water was heated to 80° C. and 3.4 g of gelatin was dissolved. To this solution, 21.7 g of leuprorelin acetate was added, followed by filtration and subsequent freeze drying. 21 g of this dry powder was dissolved in 18 ml of distilled water under heating. To this solution, 383.3 g of a dichloromethane solution containing lactic acid-glycolic acid copolymer (hereafter referred to as PLGA) [lactic acid/glycolic acid=75/25 (mol %), weight-average molecular weight: 14000] (143.3 g), separately dissolved and filtered, was added, followed by stirring emulsification for 8 minutes using the autominimixer (rotation rate: 6000 rpm) and temperature adjustment to 18° C. This emulsion was added to 30 L of a 0.1% aqueous solution of polyvinyl alcohol (PVA), previously dissolved, filtered and adjusted to the same temperature as above, followed by re-emulsification using the homomiclineflow (Tokushu Kika) at a mixer rotation rate of about 7000 rpm. The resulting w/o/w emulsion was gently stirred for about 3 hours to remove the solvent (in-water drying method).

The thus-obtained microspheres were passed through a 74 μm sieve to remove coarse particles, followed by filtration or centrifugation, to separate fine particles, which were then washed with distilled water to remove the free drug and PVA, after which they were dispersed in 356 ml of an aqueous solution of 23.2 g of D-mannitol and passed through a 250 μm and 90 μm sieves. The dispersion was spread over a tray, dispensed, and freeze dried. Drying rack temperature was gradually increased; drying was conducted for 68 hours at a final temperature of 52° C. This dry product was passed through a sieve and milled to yield a microsphere powder. This operation yielded 160 g of a microsphere powder containing 14% D-mannitol.

REFERENCE EXAMPLE 2

4 g of compound A was dissolved in 4 ml of distilled water. To this solution, 82.6 g of a dichloromethane solution containing PLGA [lactic acid/glycolic acid=75/25 (mol %), weight-average molecular weight: 11000] (30.4 g), separately dissolved and filtered, was added, followed by stirring emulsification for 5 minutes using the autominimixer (rotation rate: about 6000 rpm) and temperature adjustment to 17° C. This emulsion was added to 6.8 L of a 0.1% aqueous solution of polyvinyl alcohol (PVA), previously dissolved, filtered and adjusted to the same temperature as above, followed by emulsification in the same manner as in Reference Example 1 and subsequent gentle stirring for about 3 hours to remove the solvent (in-water drying method).

The thus-obtained microspheres were treated in the same manner as in Reference Example 1 to separate fine particles, which were then re-dispersed in a small amount of water; 9 g of D-mannitol was dissolved in this dispersion, followed by sieving and freeze drying. Drying rack temperature was gradually increased; drying was conducted for 68 hours at a final temperature of 43° C. This dry product was passed through a sieve and milled to yield a microsphere powder. This operation yielded about 35 g of a microsphere powder containing 30% D-mannitol.

REFERENCE EXAMPLE 3

7.5 g of free protirelin (TRH) was dissolved in 13 ml of distilled water. To this solution, a solution of 100 g of PLGA [lactic acid/glycolic acid=75/25 (mol %), weight-average molecular weight; 14000] in 125 ml of dichloromethane, separately dissolved and filtered, was added, followed by stirring emulsification for 5 minutes using the autominimixer (rotation rate: 5000–6000 rpm) and temperature adjustment to 18° C. This emulsion was added to 25 L of a 0.1% aqueous solution of polyvinyl alcohol (PVA), previously dissolved, filtered and adjusted to the same temperature as above, followed by emulsification in the same manner as in Reference Example 1 and subsequent gentle stirring for about 3 hours to remove the solvent (in-water drying method).

The thus-obtained microspheres were treated in the same manner as in Reference Example 1 to separate fine particles, which were then re-dispersed in a small amount of water; 15.2 g of D-mannitol was dissolved in this dispersion, followed by sieving and freeze drying. Drying rack temperature was gradually increased; drying was conducted for 91 hours at a final temperature of 50° C. This dry product was passed through a sieve and milled to yield a microsphere powder. This operation yielded about 100 g of a microsphere powder containing 15% D-mannitol.

REFERENCE EXAMPLE 4

60 mg of methotrexate and 900 mg of arginine were dissolved in 3 ml of distilled water. To this solution, a solution of 30 g of PLGA [lactic acid/glycolic acid=75/25 (mol %), weight-average molecular weight: 14000] in 48 g of dichloromethane, separately dissolved and filtered, was added, followed by stirring emulsification for 6 minutes using the autominimixer (rotation rate: about 6000 rpm) and temperature adjustment to 18° C. This emulsion was added to 3 L of a 0.1% aqueous solution of polyvinyl alcohol (PVA), previously dissolved, filtered and adjusted to the same temperature as above, followed by emulsification in the same manner as in Reference Example 1 and subsequent gentle stirring for about 3 hours to remove the solvent (in-water drying method).

The thus-obtained microspheres were treated in the same manner as in Reference Example 1 to separate fine particles, which were then re-dispersed in a small amount of water; 6.2 g of D-mannitol was dissolved in this dispersion, followed by sieving and freeze drying. Drying rack temperature was gradually increased; drying was conducted for 48 hours at a final temperature of 50° C. This dry product was passed through a sieve and milled to yield a microsphere powder. This operation yielded about 30 g of a microsphere powder containing 20% D-mannitol.

REFERENCE EXAMPLE 5

In substantially the same manner as Example 1, microspheres comprising leuprorelin acetate (11.25 mg), polylactic acid (weight-average molecular weight: 13,000–18,000) (99.3 mg) and mannitol (19.45 mg) are produced. The obtained microspheres are filled in a glass vial (volume 9 ml). This process is carried out aseptically using sterilized raw materials and materials.

In the meantime, carboxymethylcellulose sodium (10 mg), mannitol (100 mg) and polysorbate 80 (2 mg) are dissolved in an appropriate amount of distilled water for injection, which is, if necessary, subjected to pH adjustment of 5.0–7.5, in accordance with conventional production method of an injectable preparation, to yield a dispersant (total volume 2 ml). The obtained dispersant is filled in a glass ampoule (volume 2 ml). The obtained dispersant is sterilized using steam to obtain a product.

With the above-described microspheres and dispersant, an injectable preparation comprising leuprorelin acetate (11.25 mg) dispersed in 2 ml or 1 ml of a dispersant is produced.

REFERENCE EXAMPLE 6

In substantially the same manner as Example 1, microspheres comprising leuprorelin acetate (22.5 mg), polylactic acid (weight-average molecular weight: 13,000–18,000) (198.6 mg) and mannitol (38.9 mg) are produced. The obtained microspheres are filled in a glass vial (volume 9 ml). This process is carried out aseptically using sterilized raw materials and materials.

In the meantime, a dispersant (total volume 2 ml) is produced in the same manner as in Reference Example 5. The obtained dispersant is filled in a glass ampoule (volume 2 ml). The obtained dispersant is sterilized using steam to obtain a product.

With the above-described microspheres and dispersant, an injectable preparation comprising leuprorelin acetate (11.25 mg, 22.5 mg or 30 mg) dispersed in 1.5 ml of a dispersant is produced.

EXAMPLE 1

5.8 g of leuprorelin acetate was dissolved in 6.7 ml of distilled water. To this solution, 138 g of a dichloromethane solution containing polylactic acid (weight-average molecular weight: 15000) (51.6 g), separately dissolved and filtered, was added, followed by stirring emulsification for 9 minutes using the autominimixer (rotation rate: about 6000 rpm) and temperature adjustment to 15° C. This emulsion was added to 13.5 L of a 0.1% aqueous solution of polyvinyl alcohol (PVA), previously dissolved, filtered and adjusted to the same temperature as above, followed by emulsification in the same manner as in Reference Example 1 and subsequent gentle stirring for about 3 hours to remove the solvent (in-water drying method).

The thus-obtained microspheres were treated in the same manner as in Reference Example 1 to separate fine particles, which were then re-dispersed in a small amount of water; 8.7 g of D-mannitol was dissolved in this dispersion, followed by sieving and freeze drying. Drying rack temperature was gradually increased; drying was conducted for 69 hours at a final temperature of 52° C. This dry product was passed through a sieve and milled to yield a microsphere powder. This operation yielded 58 g of a microsphere powder containing 15% D-mannitol.

The effects of concentration of D-mannitol added as a sugar on changes over time in microsphere particle diameter and dispersibility are assessed below.

EXPERIMENTAL EXAMPLE 1

Microspheres containing 9.1% leuprorelin were prepared by the method of Reference Example 1. Specifically, 400 mg of leuprorelin and 565 mg of gelatin were dissolved in 0.5 ml of distilled water; to this solution, a solution of 4 g of PLGA [lactic acid/glycolic acid=75/25 (mol %), weight-average molecular weight: 14000] in 5 ml of dichloromethane was added, followed by emulsification, to yield a w/o emulsion. This emulsion was added to 1 L of a 0.25% PVA solution, followed by emulsification, to yield a w/o/w emulsion, which was gently stirred for 3 hours to cause in-water drying.

The dry product was washed with distilled water, then dispersed in a given amount of an aqueous solution of D-mannitol and freeze dried. The dispersion was then dried under reduced pressure at 40° C. for 1 day and at 50° C. for 3 days, after which it was passed though a 420 $\mu$m sieve and gently milled. 100 mg of each microsphere powder was filled in a vial; the vial was sealed with a thoroughly dried rubber stopper and kept standing in a constant-temperature chamber at 40° C. Samples were then taken periodically and assayed for particle size distribution change together with samples stored at 4° C., using a Coulter Multisizer (Coulter). The powder was dispersed in a dispersant to 5–10%; weight-average particle diameter was determined with 19.44 $\mu$m polystyrene particles as reference substance.

The particle diameter ($\mu$m) determination results are shown in the table below.

TABLE 1

| Amount of D-mannitol Added (%) | Initial Value | 40° C. | | |
|---|---|---|---|---|
| | | 1 Week | 2 Weeks | 4 Weeks |
| 0 | 36.1 | 45.5 | 46.9 | 50.5 |
| 7.5 | 26.5 | 27.6 | 29.5 | 33.6 |
| 15 | 25.7 | 26.1 | 28.0 | 31.5 |

(Unit: $\mu$m)

The values obtained after storage at 4° C. for 4 weeks were taken as the initial values and are assumed to represent particle diameters after thermal drying at about 50° C. In other words, the thermal change during the thermal drying process for microsphere production was significantly suppressed by the addition of 7.5% D-mannitol, resulting in the suppression of a particle diameter increase of about 10 $\mu$m. This effect was enhanced when the D-mannitol was added at 15% but did not significantly differ from the figure obtained when D-mannitol was added at 7.5%.

Regarding the changes during storage at 40° C., particle diameter increased in all cases; in the absence of D-mannitol, particle diameter increased by as much as 14.4 μm, while particle diameter increase was suppressed to 7.1 μm and 5.8 μm when D-mannitol was added at 7.5% and 15%, respectively. These results demonstrate that D-mannitol addition suppresses particle aggregation and prevents particle aggregation over time at 40° C., despite the fact that the heating temperature during this drying was higher than the glass transition temperature of the microspheres.

EXPERIMENTAL EXAMPLE 2

For microspheres of compound A as prepared by the method described in Reference Example 2, containing 15.0%, 27.1% and 31.4% D-mannitol, respectively, appearance and particle diameter were assessed with samples just after production and after 3 weeks of storage at 40° C. and 75% RH (Relative Humidity).

The results are shown in the table below.

TABLE 2

| Amount of D-mannitol Contained | Storage | Compound A Content % | Appearance*[1] | Particle Diameter*[2] μm ± SD |
|---|---|---|---|---|
| 15.0 | Initial | 6.55 | − | 20.5 ± 13.4 |
|  | 40° C. × 3 W | undetermined | + | 46.1 ± 28.4 |
| 27.1 | Initial | 5.65 | − | 21.0 ± 13.5 |
|  | 40° C. × 3 W | undetermined | ± to + | 28.0 ± 17.9 |
| 31.4 | Initial | 5.29 | − | 20.7 ± 13.0 |
|  | 40° C. × 3 W | undetermined | ± | 25.1 ± 16.3 |

*[1]−: No aggregation ±: Slight aggregation +: Moderate aggregation ++: Marked aggregation
*[2]Vigorously stirred manually in isotone (ultrasonication not used)

For the microspheres freeze dried at a final temperature of 43° C., higher than the glass transition temperature, 20–21 μm fine particles were stably obtained, provided that the D-mannitol content was not lower than 15%. Regarding the storage stability of these microspheres, particle diameter increased by 25.6 μm after 3 weeks of storage at 40° C. at a D-mannitol content of 15%, but this aggregation was suppressed by increasing the D-mannitol content; when the D-mannitol was added at 31.4%, aggregation was suppressed to the extent of a particle size increase of as small as 4.4 μm.

These experiments demonstrated that addition of a sugar causes marked suppression of microsphere aggregation during production and storage, and microspheres having unexpectedly good dispersibility and dispersion stability are obtained.

According to the production method of the present invention, particle binding or aggregation during freeze drying can be suppressed, enabling heating at the glass transition temperature of microspheres or higher, which in turn makes it possible to almost perfectly remove the water and organic solvent in microspheres.

Also, according to the production method of the present invention, it is possible to obtain a sustained-release preparation for injection which is sufficiently high in drug entrapment ratio and drug content without the use of a drug-retaining substance.

Further, combination of polylactic acid, addition of a sugar and heating at the glass transition temperature of microspheres or higher makes it possible to obtain a sustained-release preparation for injection which is able to release a drug for a long term (e.g., 3 months or more) in an almost zero order.

The sustained-release preparation for injection of the present invention can be stably stored at room temperature for a long period of time because of suppression of microsphere particle aggregation.

What we claim is:

1. A method of producing a sustained-release preparation for injection having a mean diameter of 10 to 40 μm which comprises 1) providing microspheres which are obtained by
      a) adding a solution containing leuprorelin acetate to a solution containing a polylactic acid having a weight-average molecular weight of about 10,000 to about 20,000 and a degree of dispersion of the polylactic acid is 1.5 to 3.5 to provide a w/o emulsion wherein the ratio of leuprorelin acetate to polylactic acid is about 0.1 to 1% (w/w);
      b) adding the w/o emulsion to a 0.05 to 10% aqueous solution of polyvinyl alcohol to provide a w/o/w emulsion;
   2) adding D-mannitol to the microspheres in an amount of about 5 to about 40% (w/w) relative to the microspheres; and
   3) freeze drying subsequent heating the microspheres at a temperature ranging from the glass transition temperature of the microspheres to a temperature which is about 10° C. higher than the glass transition temperature for about 69 to about 72 hours.

2. A method for improving a sustained release of a preparation for injection, having a diameter of 10 to 40 μm which comprises 1) providing microspheres which are obtained by
      a) adding a solution containing leuprorelin acetate to a solution containing a polylactic acid having a weight-average molecular weight of about 10,000 to about 20,000 and a degree of dispersion of the polylactic acid is 1.5 to 3.5 to provide a w/o emulsion wherein the ratio of leuprorelin acetate to polylactic acid is about 0.1 to 1% (w/w);
      b) adding the w/o emulsion to a 0.05 to 10% aqueous solution of polyvinyl alcohol to provide a w/o/w emulsion;
   2) adding D-mannitol to the microspheres in an amount of about 5 to about 40% (w/w) relative to the microspheres; and
   3) freeze drying subsequent heating the microspheres at a temperature ranging from the glass transition temperature of the microspheres to a temperature which is about 10° C. higher than the glass transition temperature for about 69 to about 72 hours.

3. The method according to claim 1, wherein the microspheres are obtained by an in-water drying method.

* * * * *